(12) United States Patent
Whitehurst et al.

(10) Patent No.: US 8,401,634 B2
(45) Date of Patent: *Mar. 19, 2013

(54) TREATMENT OF MOVEMENT DISORDERS BY BRAIN STIMULATION

(75) Inventors: Todd K. Whitehurst, Santa Clara, CA (US); James P. McGivern, Stevenson Ranch, CA (US); Kelly H. McClure, Simi Valley, CA (US)

(73) Assignee: Boston Scientific Neuromodulation Corporation, Valancia, CA (US)

( * ) Notice: Subject to any disclaimer, the term of this patent is extended or adjusted under 35 U.S.C. 154(b) by 290 days.

This patent is subject to a terminal disclaimer.

(21) Appl. No.: 12/873,170

(22) Filed: Aug. 31, 2010

(65) Prior Publication Data

US 2010/0331807 A1 Dec. 30, 2010

Related U.S. Application Data

(63) Continuation of application No. 11/641,977, filed on Dec. 19, 2006, now abandoned, which is a continuation of application No. 10/428,744, filed on May 2, 2003, now Pat. No. 7,151,961.

(60) Provisional application No. 60/383,316, filed on May 24, 2002.

(51) Int. Cl.
*A61N 1/00* (2006.01)

(52) U.S. Cl. ........................................ 607/2; 604/891.1

(58) Field of Classification Search .................. 607/2, 3, 607/45, 48; 604/891.1, 66; 600/595
See application file for complete search history.

(56) References Cited

U.S. PATENT DOCUMENTS

| | | | |
|---|---|---|---|
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |

(Continued)

FOREIGN PATENT DOCUMENTS

| | | |
|---|---|---|
| WO | WO 98/43700 A1 | 3/1998 |
| WO | WO 98/43701 A1 | 3/1998 |

(Continued)

OTHER PUBLICATIONS

Bradley et al., "Activation of Group II Metabotropic Glutamate Receptors Inhibits Synaptic Excitation of the Substantial Nigra Pars Reticulata", The Journal of Neuroscience; vol. 20(9); May 1, 2000; pp. 3085-3094.

(Continued)

*Primary Examiner* — Mark W Bockelman
(74) *Attorney, Agent, or Firm* — Vista IP Law Group LLP

(57) ABSTRACT

Systems for treating a movement disorder include a system control unit configured to be implanted at least partially within a patient and to generate at least one stimulus in accordance with one or more stimulation parameters adjusted to treat the movement disorder. The systems further include a programmable memory unit in communication with the system control unit and programmed to store the one or more stimulation parameters to at least partially define the stimulus such that the stimulus is configured to treat the movement disorder. A means for applying the stimulus to one or more stimulation sites within the patient is operably connected to the system control unit.

21 Claims, 11 Drawing Sheets

U.S. PATENT DOCUMENTS

| | | | |
|---|---|---|---|
| 4,210,139 A | 7/1980 | Higuchi | |
| 4,327,725 A | 5/1982 | Cortese et al. | |
| 4,360,019 A | 11/1982 | Portner et al. | |
| 4,487,603 A | 12/1984 | Harris | |
| 4,627,850 A | 12/1986 | Deters et al. | |
| 4,692,147 A | 9/1987 | Duggan | |
| 4,702,254 A | 10/1987 | Zabara | |
| 4,725,852 A | 2/1988 | Gamblin et al. | |
| 4,867,164 A | 9/1989 | Zabara | |
| 5,025,807 A | 6/1991 | Zabara | |
| 5,193,539 A | 3/1993 | Schulman et al. | |
| 5,193,540 A | 3/1993 | Schulman et al. | |
| 5,312,439 A | 5/1994 | Loeb | |
| 5,683,422 A | 11/1997 | Rise | |
| 5,707,396 A | 1/1998 | Benabid | |
| 5,711,316 A * | 1/1998 | Elsberry et al. | 128/898 |
| 5,716,377 A * | 2/1998 | Rise et al. | 607/2 |
| 5,792,186 A * | 8/1998 | Rise | 607/2 |
| 5,832,932 A * | 11/1998 | Elsberry et al. | 128/898 |
| 5,833,709 A * | 11/1998 | Rise et al. | 607/2 |
| 6,016,449 A | 1/2000 | Fischell et al. | |
| 6,051,017 A | 4/2000 | Loeb et al. | |
| 6,094,598 A * | 7/2000 | Elsberry et al. | 607/116 |
| 6,164,284 A | 12/2000 | Schulman et al. | |
| 6,185,452 B1 | 2/2001 | Schulman et al. | |
| 6,205,359 B1 | 3/2001 | Boveja | |
| 6,208,894 B1 | 3/2001 | Schulman et al. | |
| 6,227,203 B1 | 5/2001 | Rise et al. | |
| 6,356,784 B1 | 3/2002 | Lozano et al. | |
| 6,415,184 B1 | 7/2002 | Ishikawa et al. | |
| 6,463,328 B1 | 10/2002 | John | |
| 6,464,687 B1 | 10/2002 | Ishikawa et al. | |
| 6,782,292 B2 | 8/2004 | Whitehurst | |
| 6,788,975 B1 | 9/2004 | Whitehurst et al. | |
| 7,151,961 B1 * | 12/2006 | Whitehurst et al. | 607/2 |
| 2001/0003799 A1 | 6/2001 | Boveja | |
| 2002/0013612 A1 | 1/2002 | Whitehurst | |
| 2002/0161403 A1 | 10/2002 | Meadows et al. | |
| 2003/0036780 A1 | 2/2003 | Barrett et al. | |
| 2004/0172089 A1 | 9/2004 | Whitehurst et al. | |
| 2006/0241717 A1 | 10/2006 | Whitehurst et al. | |

FOREIGN PATENT DOCUMENTS

| | | |
|---|---|---|
| WO | WO 98/37926 A1 | 9/1998 |
| WO | WO 00/38669 A2 | 7/2000 |
| WO | WO 00/38669 A3 | 7/2000 |
| WO | WO 01/60450 A1 | 8/2001 |

OTHER PUBLICATIONS

Cameron et al., "Micromudular Implants to Provide Electrical Stimulation of Paralyzed Muscles and Limbs", IEEE Transaction on Biomedical Engineering; vol. 44; No. 9; Sep. 1997; pp. 781-790.

Gill et al., "Direct Brain Infusion of Blial Cell Line-Derived Neurotrophic Factor in Parkinson Disease"; Nature Medicine; Advance Online Publication; Mar. 31, 2003.

Handforth et al., "Suppression of Harmaline-Induced Tramor in Rats by Vagus Nerve Stimulation"; Movement Disorders; vol. 16(1); Jan. 2001; pp. 84-88.

Hooper et al., "A Prospective Study of Thalamic Deep Brain Stimulation for the Treatment of Movement Disorders in Multiple Sclerosis"; British Journal of Neurosurgery; vol. 16; No. 2; Apr. 1, 2002; pp. 249-260.

Levy et al., "Effects of Apomorphine on Subthalamic Nucleus and Globus Pallidus Internus Neurons in Patients with Parkinson's Disease"; Journal of Neurophysiology; vol. 86(1); Jul. 2001; pp. 249-260.

Stefan et al., "Subdyskinetic Aomorphine Responses in Globus Pallidus and Subthalamus of Parkinsonian Patients: Lack of Clear Evidence for the 'Indirect Pathway'"; Clinical Nuerophysiology; vol. 113(1); Jan. 2002; pp. 91-100.

Walker et al., "Regulation of Limbic Motor Seizurs by GABA and Glutamate Transmission in Nucleus Tractus Solitarius"; Epilepsia; vol. 40(8); Aug. 1999; pp. 1051-1057.

Whitehurst, McGivern and Kuzma inventors for AB-116U; U.S. Appl. No. 10/081,820, filed Feb. 19, 2002; Entitled "Fully Implantable Miniature Neurostimulator for Vagus Nerve Stimulator".

Whitehurst and McGivern inventors for AB-134U; U.S. Appl. No. 10/224,021, filed Aug. 19, 2002; Entitle "Treatment of Movement Disorders by Extradural Motor Cortex Stimulation".

Whitehurst, McGivern and Kuzma inventors for AB-210U; U.S. Appl. No. 10/057,115, filed Jan. 24, 2002; Entitled "Fully Implantable Miniature Neurostimulator for Stimulation as a Therapy for Epilepsy".

Whitehurst inventor for AB-223U; U.S. Appl. No. 10/428,473, filed May 2, 2003; Entitled "Treatment of Epilepsy by Brain Stimulation".

Benabid et al., "Long-Term Suppression of Tremor by Chronic Stimulation of the Ventral Intermediate Thalamic Nucleus", Lancet, vol. 377 (8738); Feb. 16, 1991; pp. 403-406.

Handforth et al., "Effect on Vagus Nerve Stimulation of Essential Tremo"; Neurology; vol. 54; Suppl. 3; 2000; pp. A238.

* cited by examiner

TREATMENT OF MOVEMENT DISORDERS BY BRAIN STIMULATION

RELATED APPLICATIONS

The present application is a continuation of U.S. patent application Ser. No. 11/641,977, filed Dec. 19, 2006, which application is a continuation of U.S. application Ser. No. 10/428,744, filed May 2, 2003, which application claims the benefit of U.S. Provisional Application Ser. No. 60/383,316, filed May 24, 2002, which applications are incorporated herein by reference in their entireties.

BACKGROUND

Movement disorders are neurologic syndromes characterized by either an excess or a paucity of movement. These disorders affect approximately two million Americans, including over one million suffering from benign essential tremor, and half a million suffering from Parkinson's Disease. A substantial percentage of those afflicted with movement disorders experience a significant decrease in quality of life, suffering such problems as incapacitating tremor, limited mobility, bradykinesia (difficulty consciously initiating movement), dysarthria (difficulty with speech), and consequent social isolation. The etiology of many movement disorders, e.g., benign essential tremor, is poorly understood. For other movement disorders, e.g., Parkinson's disease, the mechanism of the disorder and brain cells affected have been identified, but even with optimal care the disease may not be reversed and may even continue to progress.

Parkinson's Disease is caused by a gradual loss of dopaminergic (i.e., dopamine-secreting) neurons in the substantia nigra. Consequently, levels of dopamine decrease in the striatum (i.e., the putamen and the caudate nucleus). Although dopamine has both excitatory and inhibitory effects on the striatum, the predominant effect of the loss of dopamine is decreased inhibition (by GABA) of the internal segment of the globus pallidus. This leads to increased GABA output from the internal segment of the globus pallidus, which inhibits the ventrolateral thalamus. This leads in turn to decreased inhibition of (and ultimately decreased control over) the motor cortex. The subthalamic nucleus appears to increase its activity in Parkinson's Disease as well, and this is believed to contribute to the symptoms of the disease.

Essential Tremor (ET), a.k.a., Benign Essential Tremor, is the most common movement disorder. It is a syndrome characterized by a slowly progressive postural and/or kinetic tremor, usually affecting both upper extremities. The prevalence of ET in the US is estimated at 0.3-5.6% of the general population. A 45-year study of ET in Rochester, Minn. reported an age- and gender-adjusted prevalence of 305.6 per 100,000 and an incidence of incidence of 23.7 per 100,000.

ET affects both sexes equally. The prevalence of ET increases with age. There are bimodal peaks of onset—one in late adolescence to early adulthood and a second peak in older adulthood. The mean age at presentation is 35-45 years. ET usually presents by 65 years of age and virtually always by 70 years. Tremor amplitude slowly increases over time. Tremor frequency decreases with increasing age. An 8 12 Hz tremor is seen in young adults and a 6 8 Hz tremor is seen in the elderly. Although ET is progressive, no association has been found between age of onset and severity of disability.

Disability stemming from ET is common. Significant changes in livelihood and socializing are reported by 85% of individuals with ET, and 15% report being seriously disabled due to ET. Decreased quality of life results from both loss of function and embarrassment. In a study of hereditary ET, 60% did not seek employment, 25% changed jobs or took early retirement, 65% did not dine out, 30% did not attend social functions, and 20% stopped driving.

SUMMARY

Systems for treating a movement disorder include a system control unit configured to be implanted at least partially within a patient and to generate at least one stimulus in accordance with one or more stimulation parameters adjusted to treat the movement disorder. The systems further include a programmable memory unit in communication with the system control unit and programmed to store the one or more stimulation parameters to at least partially define the stimulus such that the stimulus is configured to treat the movement disorder. A means for applying the stimulus to one or more stimulation sites within the patient is operably connected to the system control unit.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Figure 1A:
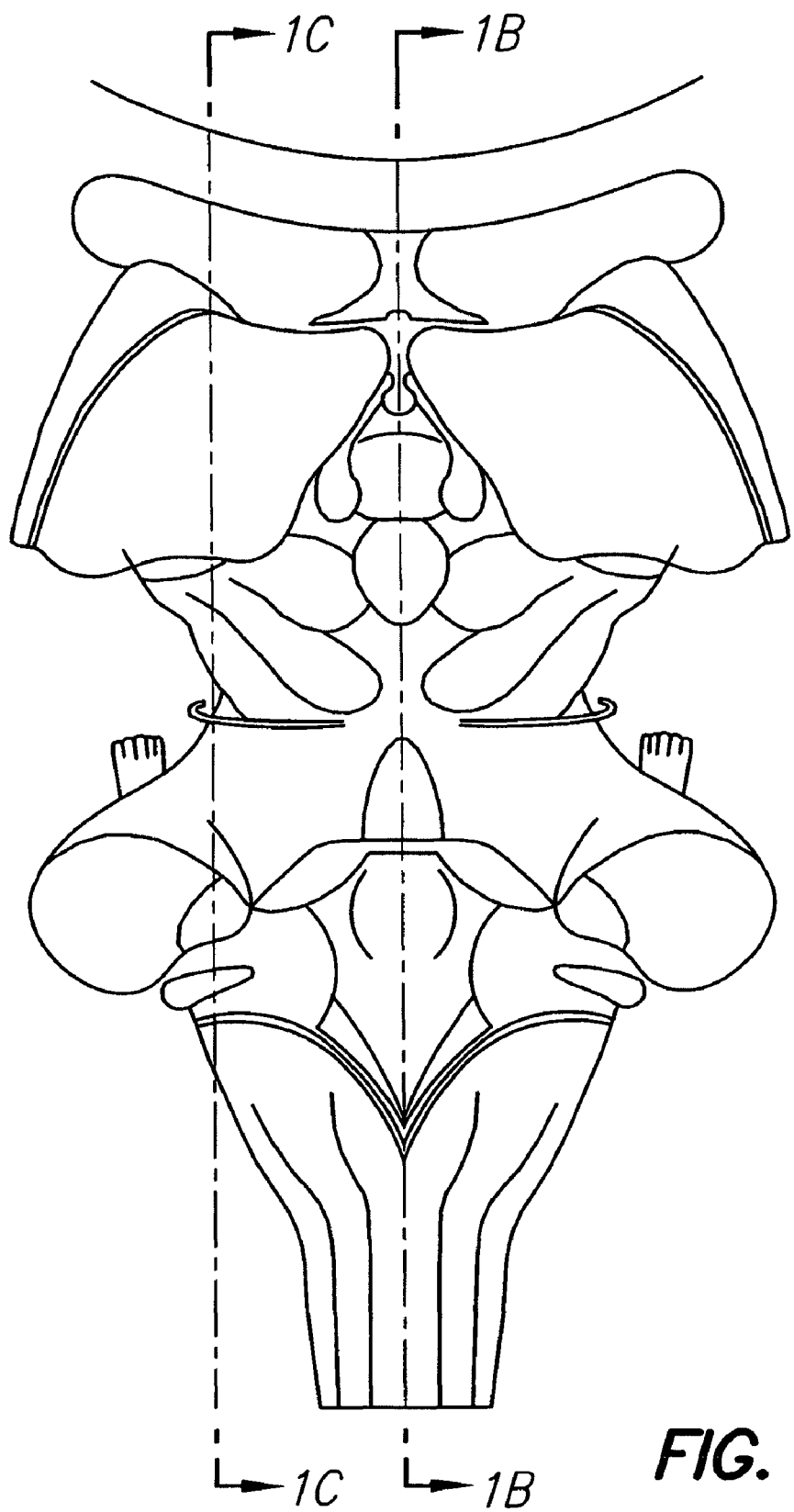
FIG. 1A depicts the dorsal surface of the brain stem according to principles described herein.

Methods and systems for treating one or more movement disorders are described herein. An implanted stimulator is configured to apply at least one stimulus to a stimulation site within a patient in accordance with one or more stimulation parameters. The stimulus is configured to treat a movement disorder and may include electrical stimulation and/or drug stimulation. As used herein, and in the appended claims, "treating" a movement disorder refers to any amelioration of one or more causes and/or one or more symptoms of the movement disorder.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

The pathophysiology of many movement disorders is unknown. For example, the cause of essential tremor ("ET") is unknown. However, it has been hypothesized that ET is the result of an abnormally functioning central oscillator, which is located in Guillain Mollaret triangle near the brainstem, and involves the inferior olivary nucleus. It is also believed that there is probable involvement of cerebellar-brainstem-thalamic-cortical circuits.

When Harmaline, a Monoamine Oxidase (MAO) inhibitor, is administered to primates with lesions of ventromedial tegmental tract or lateral cerebellum, an ET-like tremor is produced. In these animals, inferior olivary nucleus neurons file synchronously at the tremor frequency. C-2-deoxyglucose PET studies demonstrate hypermetabolism in the inferior olivary nuclei of rats and cats with harmaline-induced tremor. Stimulation of the vagus nerve helped resolve tremor in rats with harmaline-induced tremor.

In patients with ET, [$^{18}$F]-fluorodeoxyglucose PET studies identified increased glucose consumption in the medulla. [$^{15}$O]—H$_2$O PET studies demonstrate an increase in medullary regional cerebral blood flow (CBF) in subjects with ET, only after the administration of ethanol, and showed bilateral overactivity of cerebellar circuitry.

The nucleus tractus solitarius (NTS) sends fibers bilaterally to the reticular formation and hypothalamus that are important in the reflex control of cardiovascular, respiratory, and gastrointestinal functions. The NTS also provides input to the dorsal motor nucleus of the vagus that enables the parasympathetic fibers of the vagus nerve to control these reflex responses. The NTS runs the entire length of the medulla oblongata, and the NTS receives somatic sensory input from all cranial nerves, with much of its input coming from the vagus nerve. Since the NTS receives much of its input from the vagus nerve, and since electrical stimulation of the vagus nerve has been demonstrated to be effective in the treatment of an animal model of essential tremor (i.e., for harmaline-induced tremor), then electrical stimulation of the NTS may be effective in the treatment of movement disorders such as essential tremor.

Patients suffering from tremor and other symptoms may undergo surgery to lesion a part of the brain (e.g., the ventral intermediate (Vim) nucleus of the thalamus the internal segment of the globus pallidus (GPi), or the subthalamic nucleus (STN)), which may afford some relief. However, a lesion is irreversible, and may lead to side effects such as dysarthria or cognitive disturbances. Additionally, lesions generally yield effects on only one side of the body (the contra-lateral side), and bilateral lesions are significantly more likely to produce side effects. Other surgical procedures, such as fetal tissue transplants, are costly and unproven.

Other areas of the brain exhibit decreased neural activity in some patients with movement disorders. For instance, some Parkinson's disease patients demonstrate decreased neural activity in parts of the caudate and putamen, the external segment of the globus pallidus (GPe), substantia nigra, and/or parts of the thalamus.

An article published online by Gill, et al. describes delivery of glial cell line-derived neurotrophic factor (GDNF) directly into the putamen of five Parkinson patients in a phase 1 safety trial. [See Gill, et al. "Direct brain infusion of glial cell line-derived neurotrophic factor in Parkinson disease." *Nature Medicine* epub ahead of print: 2003 Mar. 31.] Baseline positron emission tomography (PET) scans indicated that the posterior segment of the putamen in all patients had low [$^{18}$F]dopa uptake. After 18 months, PET scans showed a 28% increase in putamen dopamine storage, in contrast to the predicted decline of up to 20% over this period for Parkinson disease patients. The authors note, however, that the exact mechanism by which GDNF works has yet to be established.

Levy, et al., 2001, present data based on microelectrode recordings from the GPi and the STN during administration of apomorphine, a fast-acting non-selective $D_1$-dopamine and $D_2$-dopamine receptor agonist. [See Levy, et al. "Effects of apomorphine on subthalamic nucleus and globus pallidus internus neurons in patients with Parkinson's disease." *Journal of Neurophysiology* 2001 July; 86(1):249-60.] Apomorphine has previously been demonstrated to ameliorate symptoms of Parkinson's disease. In the study, the authors administered doses of apomorphine sufficient to produce relief of Parkinson symptoms, but not sufficient to induce common side effects such as dyskinetic movements. Following baseline microelectrode recordings, apomorphine was administered. The spontaneous discharge of neurons encountered before, during, and after the effect of apomorphine had waned was also sampled.

A reduction in Parkinson symptoms (e.g., limb tremor) was observed in patients when apomorphine reached therapeutic levels. Apomorphine significantly decreased the overall firing rates of GPi neurons, but there was no change in the overall firing rate of neurons in the STN. Concurrent with a reduction in limb tremor, the percentage of cells with tremor-related activity (i.e., tremor cells) was found to be significantly reduced from 19% to 6% in the STN and from 14% to 0% in the GPi following apomorphine administration. Apomorphine also decreased the firing rate of STN tremor cells. As the effects of apomorphine waned, the overall firing rates of GPi neurons increased. In contrast to the findings above, Stefani, et al., 2002, found that administration of apomorphine did indeed reduce the firing rates of all STN cells in patients with Parkinson's disease, concurrent with a reduction in the clinical symptoms of Parkinson's disease. [See Sefani, et al., "Subdyskinetic apomorphine responses in globus pallidus and subthalamus of parkinsonian patients: lack of clear evidence for the 'indirect pathway'." *Clinical Neurophysiology* 2002 January; 113(1):91-100.] These results suggest that the discharge frequency of the GPi and possibly of the STN is a measurable quantity that correlates with the clinical efficacy of medication.

While not previously observed, this GPi discharge frequency phenomenon may occur during deep brain stimulation (DBS) as well. The subthalamic nucleus (STN) is believed to demonstrate increased neurotransmitter release in Parkinson's disease, and it responds to deep brain stimulation. Thus, it may demonstrate a similar discharge frequency phenomenon as the GPi. Since the Vim nucleus of the thalamus also responds to deep brain stimulation, it may also demonstrate a similar discharge frequency phenomenon.

In addition, high frequency chronic electrical stimulation (i.e., frequencies above 100 Hz) of certain areas of the brain has been demonstrated to be as efficacious as producing a lesion in any one of those areas. In contrast to ablation surgery, chronic electrical stimulation is reversible. Additionally, stimulation parameters may be adjusted to minimize side effects while maintaining efficacy; such "fine tuning" is unavailable when producing a lesion.

An implantable chronic stimulation device for DBS is available and similar systems are under development. DBS has proven to be effective for treating some patients with movement disorders; however, the current procedure is highly invasive, and the initial surgery for placement of the available system requires essentially an entire day. These systems require the power source and stimulation electronics to be implanted far from the electrodes, generally in the chest or elsewhere in the trunk of the body. These bulky systems therefore require extensive invasive surgery for implantation, and breakage of the long leads is highly likely. In addition, current DBS systems for movement disorders use no feedback for regulation of stimulation.

Figure 1B:
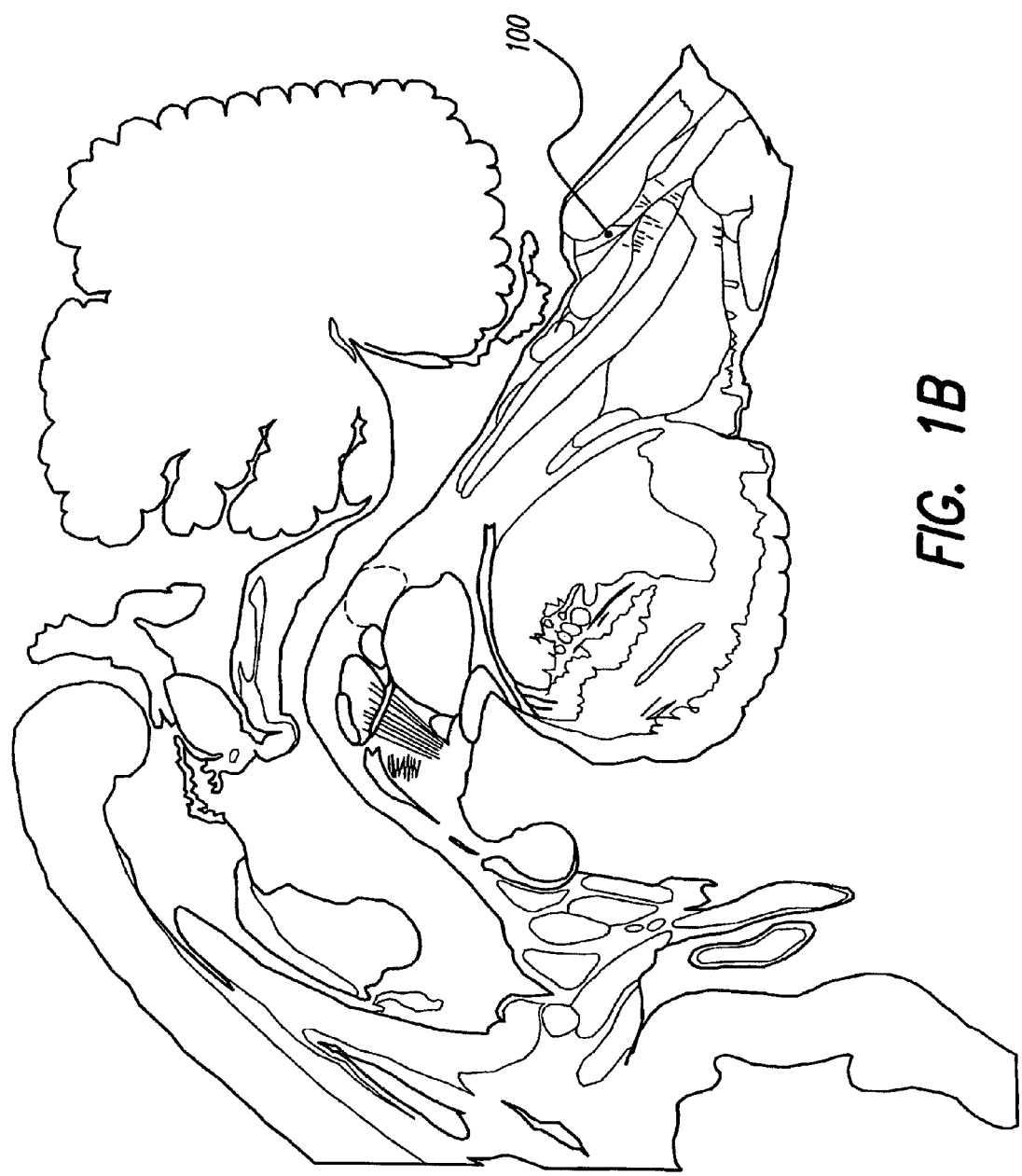
FIGS. 1B and 1C are section views through the brain stem depicted in FIG. 1A according to principles described herein.
Figure 1C:
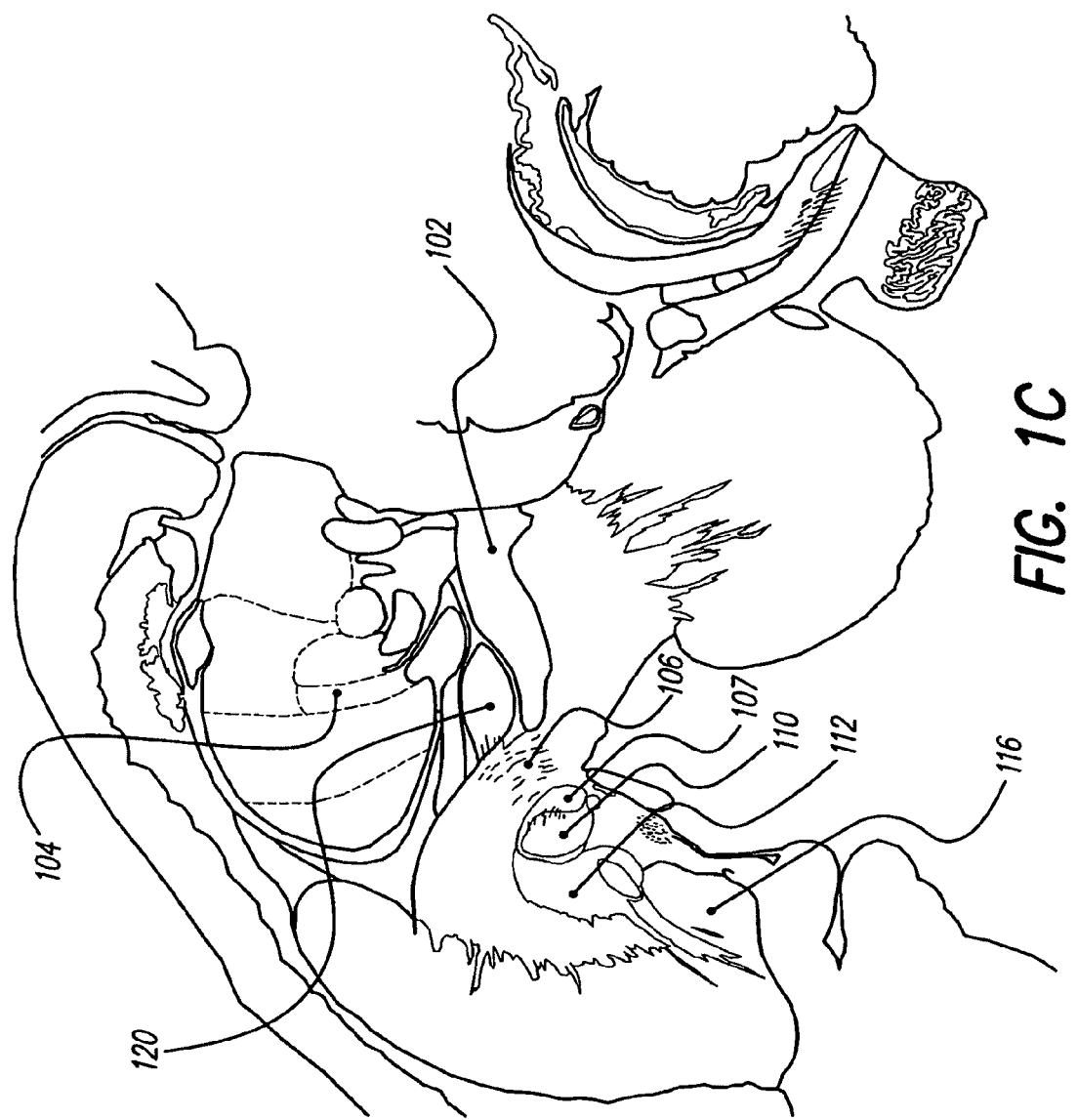
Figure 2A:
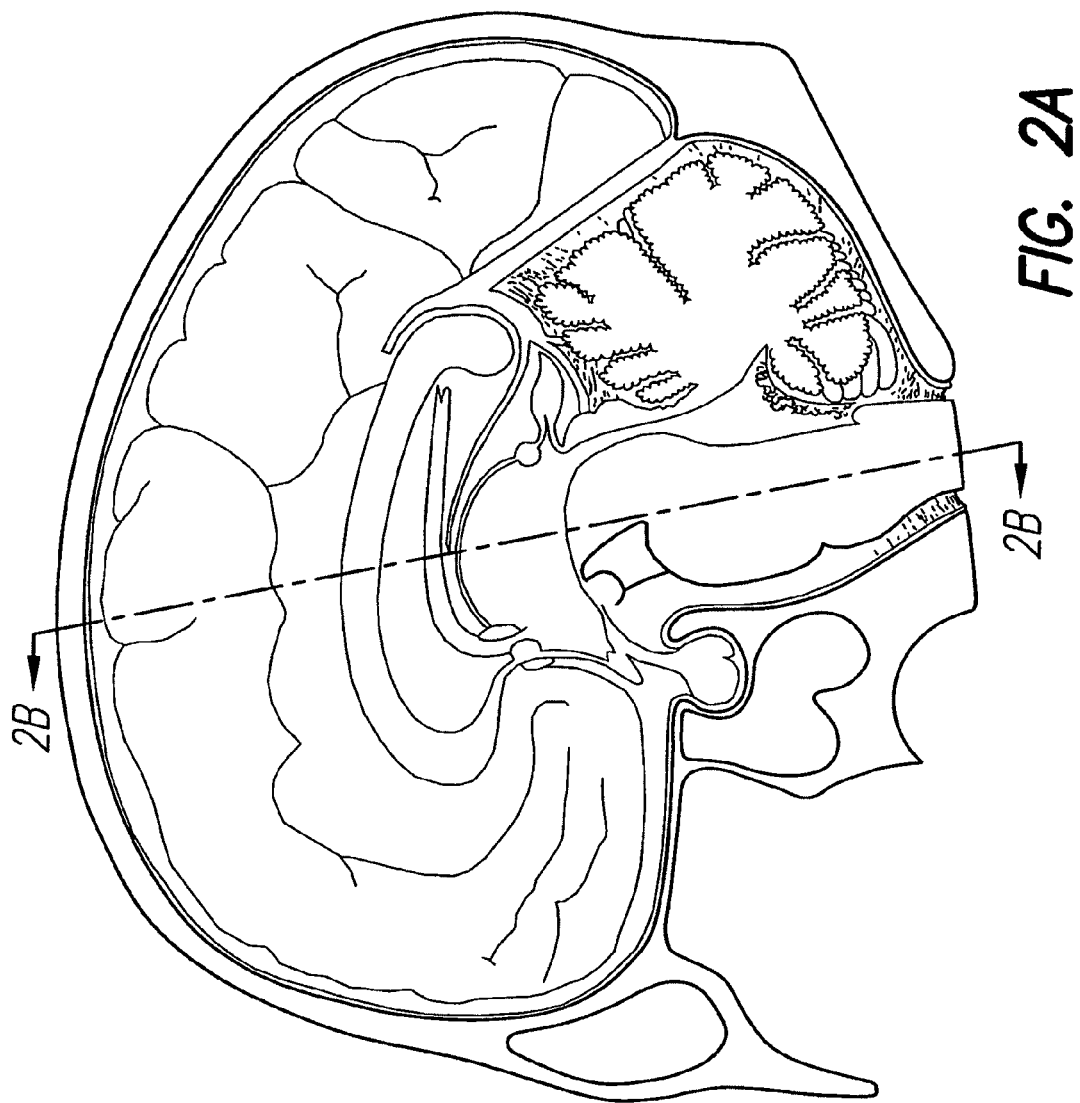
FIG. 2A depicts the medial surface of the brain according to principles described herein.
Figure 2B:
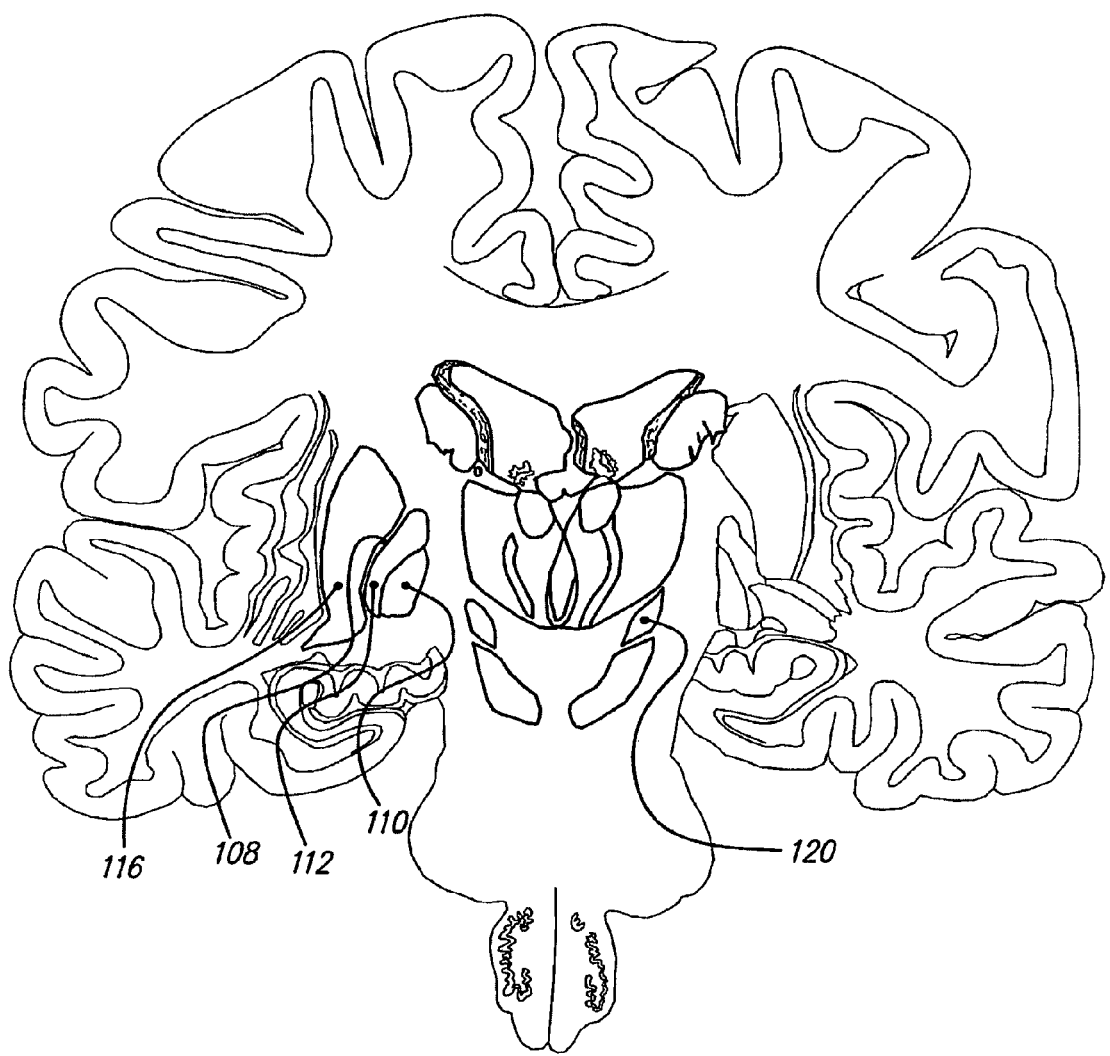
FIG. 2B is a coronal section view of the brain of FIG. 2A according to principles described herein.

FIG. 1A depicts the dorsal surface of the brain stem, and FIGS. 1B and 1C are section views through the brain stem depicted in FIG. 1A, while FIG. 2A depicts the medial surface of the brain and FIG. 2B is a coronal section view of the brain of FIG. 2A. FIG. 1B shows the location of the nucleus tractus solitarius (NTS) 100. FIG. 1C shows the locations of the substantia nigra pars reticulata 102 (as seen in the figure, the substantia nigra pars reticulata is included in the substantia nigra, as is the substantia nigra pars compacta), the ventral intermediate (Vim) thalamic nucleus 104, the pallidosubthalamic tracts 106, and the pallido-thalamic axons 107 (as seen in the figure, pallido-thalamic axons are found in the lenticular fasciculus and the ansa lenticularis). FIG. 2B shows the location of the putamen to GPe fibers 108. FIGS. 1C and 2B show the locations of the internal globus pallidus (GPi) 110, the external globus pallidus (GPe) 112, the putamen 116, and the subthalamic nucleus (STN) 120.

It is believed that applying a stimulus to one or more of the above-mentioned areas may be useful in treating one or more movement disorders. As mentioned, "treating" a movement disorder refers to any amelioration or prevention of one or more causes, symptoms, and/or sequelae of the movement disorder. Consequently, an SCU, also referred to herein as a stimulator, may be implanted within a patient to deliver a stimulus to one or more stimulation sites within the patient to treat one or more nerve compression syndromes. In some examples, the stimulus may include an electrical stimulation current and/or one or more drugs that are infused into the stimulation site.

The one or more stimulation sites referred to herein, and in the appended claims, may include, but are not limited to, the NTS, the ventral intermediate thalamic nucleus, the GPi, the GPe, the STN, the pallidosubthalamic tracts, the substantia nigra pars reticulate, the pallido-thalamic axons, the putamen to GPe fibers, the subthalamo-pallidal fibers, the putamen to GPi fibers, the cerebellum, and/or any other suitable location within the brain. In some examples, as will be described in more detail below, the stimulus is configured to adjust the level of neural activity in one or more of these areas, and thereby treat one or more movement disorders.

For instance, for patients who demonstrate increased neural activity of ventral intermediate thalamic nucleus, pallido-thalamic axons, putamen to GPe fibers, GPi, STN, sub-thalamo-pallidal fibers, and/or the cerebellum, inhibitory stimulation may be applied to one or more of these areas in order to treat one or more movement disorders. On the other hand, for patients who exhibit decreased neural activity of NTS, substantia nigra pars reticulata, pallido-subthalamic tracts, GPe, putamen, and/or putamen to GPi fibers, excitatory stimulation may be applied to one or more of these areas in order to treat one or more movement disorders. As used herein, the terms "stimulate", "stimulation", and "stimulating" refer to infusion of one or more drugs at the stimulation site and/or applying one or more electrical current pulses to the stimulation site.

As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

Herein, stimulating drugs may include medications and other pharmaceutical compounds, anesthetic agents, synthetic or natural hormones, neurotransmitters, interleukins, cytokines, lymphokines, chemokines, growth factors (e.g., glial cell line-derived neurotrophic factor (GDNF), brain cell line-derived neurotrophic factor (BDNF)), and other intracellular and intercellular chemical signals and messengers, and the like. Certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

A number of drugs have demonstrated efficacy in the treatment of Parkinson's disease. For example, a drug referred to as "Levodopa" is effective in some patients with Parkinson's disease. Levodopa is typically administered with a dopa decarboxylase inhibitor in order to prevent systemic side effects. Patent Cooperation Treaty publication WO 00/38669 (A2), which is incorporated herein by reference in its entirety, teaches administration of naloxone to the substantia nigra for the prevention of neural degeneration. (Naloxone is an opiate antagonist.) Since degeneration of the substantia nigra is the primary pathology of Parkinson's disease, administration of naloxone to the substantia nigra may be therapeutic.

In some examples, the SCU includes an implantable signal generator coupled to one or more electrodes and/or an implantable pump connected to a catheter(s). These systems deliver electrical stimulation and/or one or more stimulating drugs to specific areas in the brain. One or more electrodes are surgically implanted in the brain to provide electrical stimulation, and/or one or more catheters are implanted in the brain to infuse the stimulating drug(s).

In some examples, the SCU includes an implantable microstimulator, such as a BION® microstimulator (Advanced Bionics® Corporation, Valencia, Calif.). Exemplary microstimulators will be described in connection with FIGS. 3A-3C. Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3A:
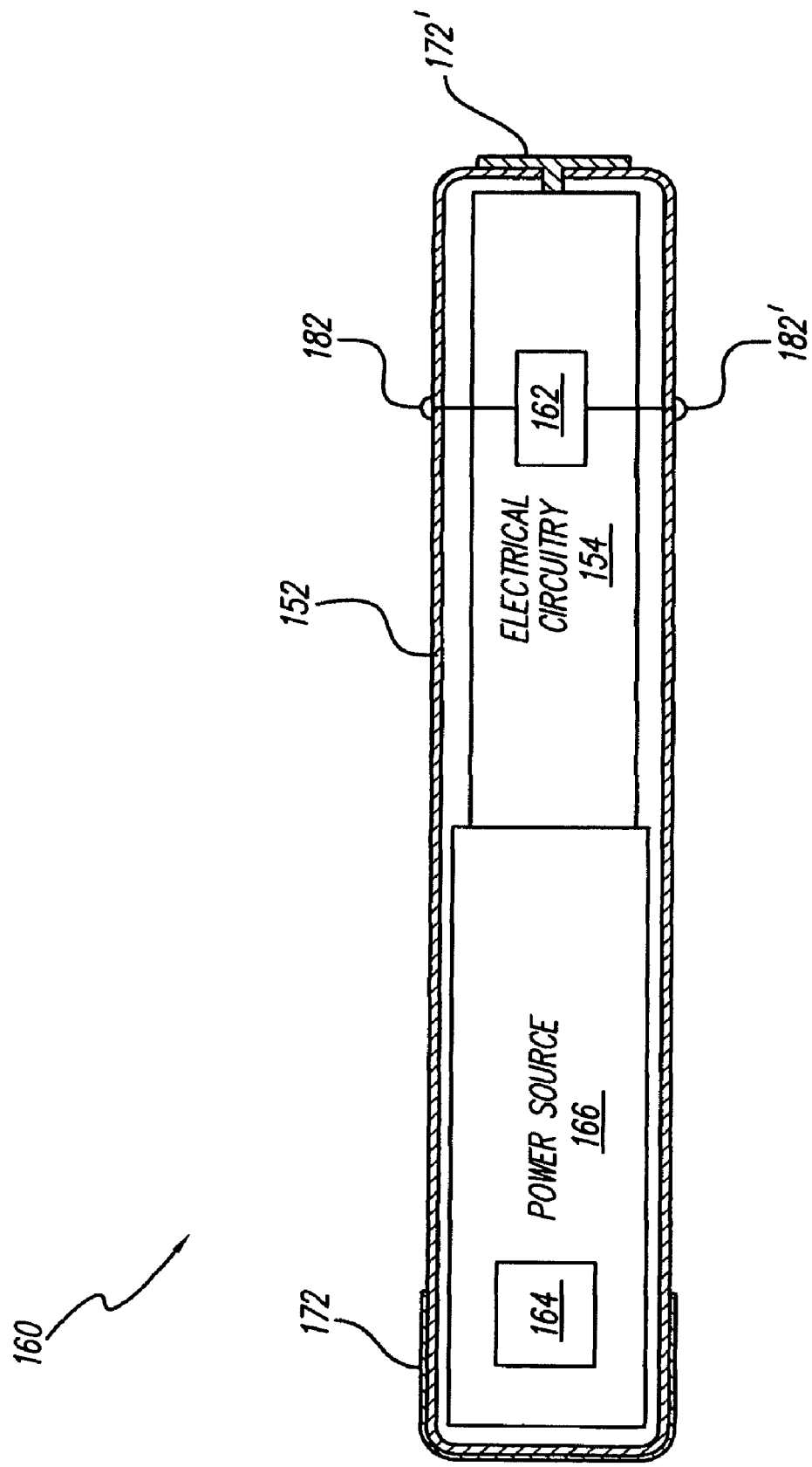
FIGS. 3A, 3B, and 3C show some possible configurations of an implantable microstimulator of the present invention according to principles described herein.
Figure 3B:
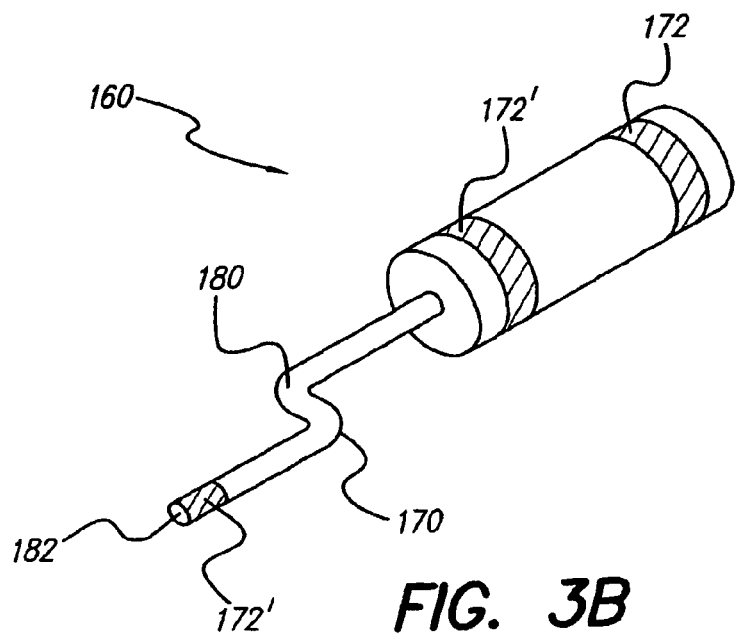
Figure 3C:
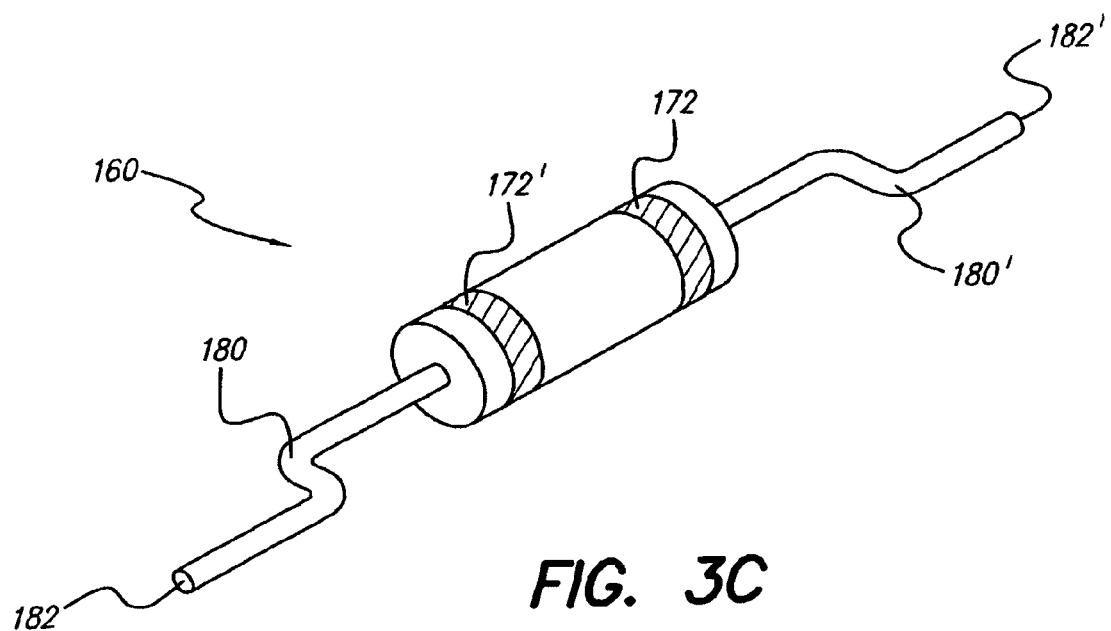

As shown in FIGS. 3A, 3B, and 3C, an exemplary microstimulator SCU 160 may include a narrow, elongated capsule 152 containing electronic circuitry 154 connected to electrodes 172 and 172', which may pass through the walls of the capsule at either end. Alternatively, electrodes 172 and/or 172' may be disposed on the outer surface or case of the SCU 160 and/or arranged on a catheter or at the end of a lead, as described below.

In some examples, electrodes 172 and 172' may include a stimulating electrode (to be placed close to the target) and an indifferent electrode (for completing the circuit). Other configurations of microstimulator SCU 160 are possible.

Certain configurations of implantable microstimulator SCU 160 are sufficiently small to permit placement in or adjacent to the structures to be stimulated. For instance, in these configurations, capsule 152 may have a diameter substantially equal to or less than 4-5 millimeters and a length substantially equal to or less than 25-35 mm. The shape of the microstimulator may be determined by the structure of the desired target, the surrounding area, and the method of implantation. A thin, elongated cylinder with electrodes at the ends, as shown in FIGS. 3A, 3B, and 3C, is one possible configuration, but other shapes, such as cylinders, disks, spheres, and helical structures, are possible, as are additional electrodes, infusion outlets, leads, and/or catheters.

Microstimulator SCU 160, when certain configurations are used, may be implanted with a surgical tool such as a tool specially designed for the purpose, or with a hypodermic needle, or the like. Alternatively, microstimulator SCU 160 may be implanted via conventional surgical methods (e.g., via a small incision), or may be placed using endoscopic or laparoscopic techniques.

In some examples, the microstimulator SCU 160 may be implanted with the aid of a stereotactic frame via a minimal surgical procedure (e.g., through a small burr hole) adjacent to or at the sites mentioned above. As mentioned, the microstimulator SCU 160 may be sufficiently small to be able to fit through a conventional burr hole in the skull. Alternative implantation methods include CT scan or ultrasound image guidance.

The external surfaces of microstimulator SCU 160 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 172 and 172' may be made of a noble or refractory metal or compound, such as platinum, iridium, tantalum, titanium, titanium nitride, niobium or alloys of any of these, in order to avoid corrosion or electrolysis which could damage the surrounding tissues and the device.

In some examples, the microstimulator SCU 160 may include two leadless electrodes disposed on an outer surface or case thereof. Alternatively, either or both electrodes 172 and 172' may alternatively be located at the ends of short, flexible leads. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s).

Figure 4:
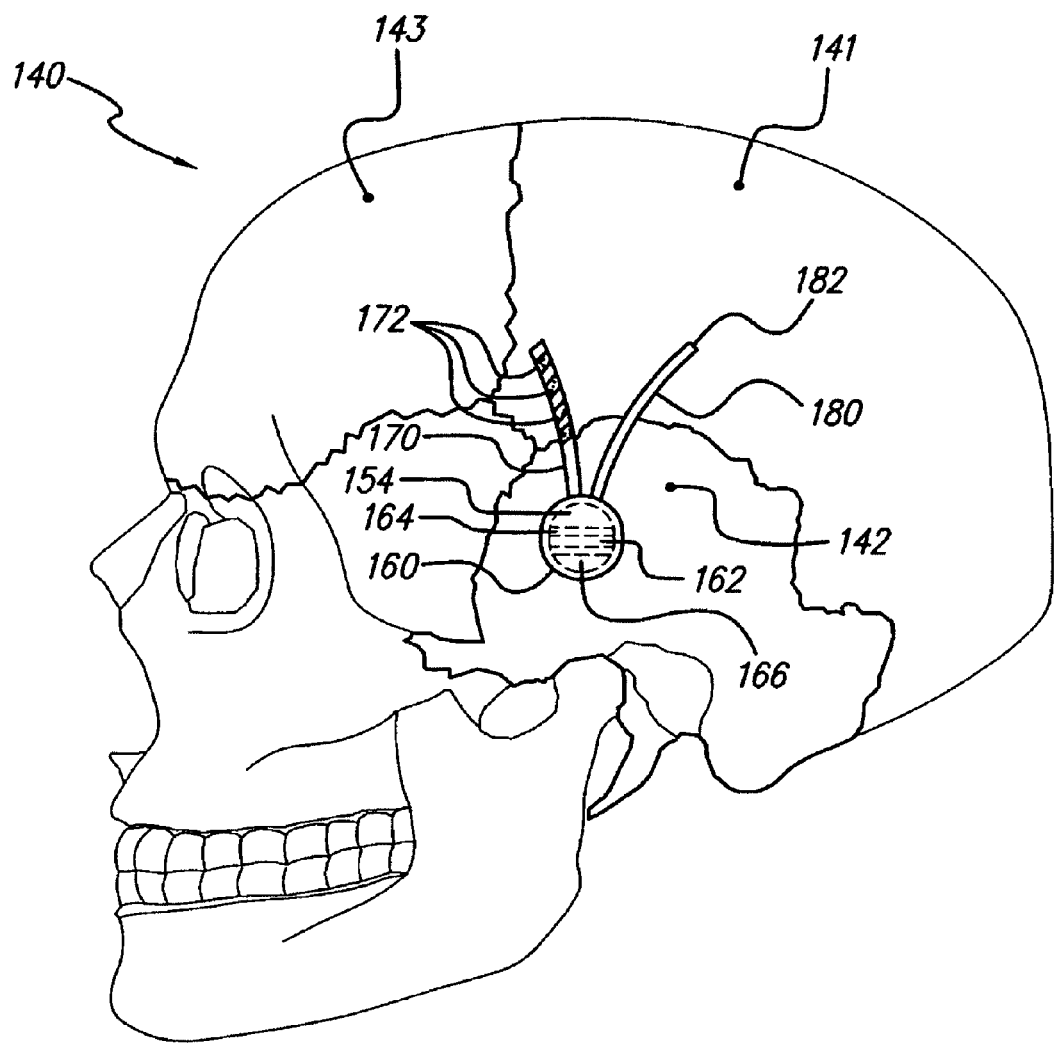
FIG. 4 illustrates a lateral view of the skull and components of an exemplary system control unit according to principles described herein.

In some examples, as depicted in FIG. 4, the SCU 160 may be implanted beneath the scalp, such as in a surgically-created shallow depression or opening in the skull 140. The surgically-created shallow depression or opening may be located in the parietal bone 141, the temporal bone 142, and/or the frontal bone 143. In some examples, the SCU 160 is configured to conform to the profile of surrounding tissue(s) and/or bone(s). This may minimize pressure applied to the skin or scalp, which pressure may result in skin erosion or infection.

As shown in FIG. 4, one or more electrode leads 170 and/or catheters 180 attached to SCU 160 run subcutaneously, for instance, in a surgically-created shallow groove(s) in the skull, to an opening(s) in the skull, and pass through the opening(s) into or onto the brain parenchyma and surrounding tissue. Recessed placement of the SCU and the lead(s) and/or catheter(s) may decrease the likelihood of erosion of the overlying skin, and may minimize any cosmetic impact.

As shown in FIG. 4, electrode(s) 172 are carried on lead 170 having a proximal end coupled to SCU 160. The lead contains insulated wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case may be made of metal (e.g. titanium) or ceramic, which materials are also, advantageously, biocompatible. In addition, SCU 160 may be configured to be Magnetic Resonance Imaging (MRI) compatible.

In some alternatives, the electrical stimulation may be provided as described in International Patent Application Serial Number PCT/US01/04417 (the '417 application), filed Feb. 12, 2001, and published Aug. 23, 2001 as WO 01/60450, which application is incorporated herein by reference in its entirety.

In the case of treatment alternatively or additionally constituting drug infusion, SCU 160 (which herein refers to IPGs, implantable pumps, IPG/pump combinations, microstimulators for drug and/or electrical stimulation, and/or other alternative devices described herein) may contain at least one pump 162 for storing and dispensing one or more drugs through outlet(s) 182/182' and/or catheter(s) 180/180' into a predetermined site(s) in the brain tissue. When a catheter is used, it includes at least one infusion outlet 182, usually positioned at least at a distal end, while a proximal end of the catheter is connected to SCU 160.

Figure 5:
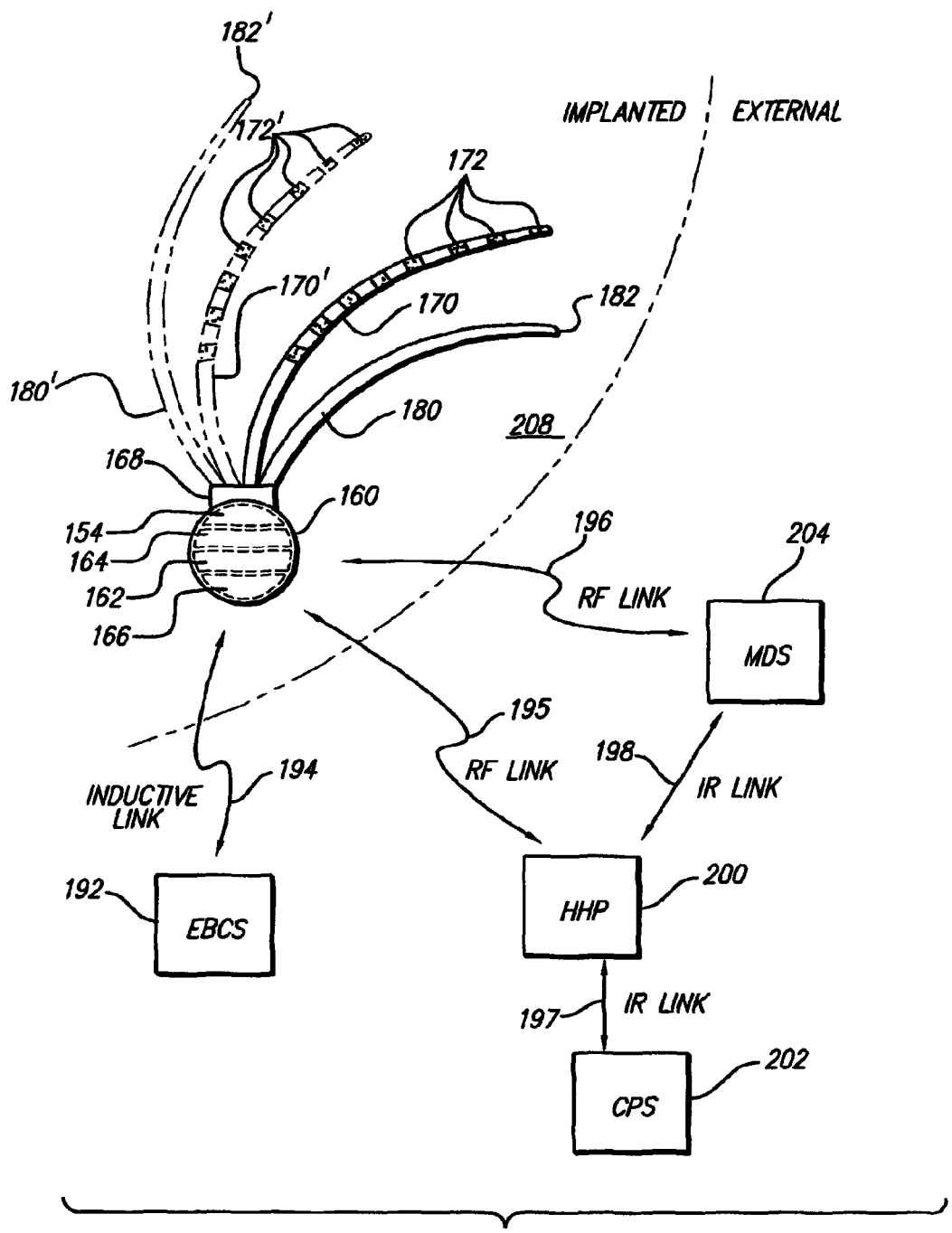
FIG. 5 illustrates internal and external components of a stimulation system according to principles described herein.

In some examples, as depicted in FIG. 5, at least one lead 170 may be coupled to SCU 160 via a suitable connector 168. Additional leads 170' and/or catheter(s) 180' may be attached to SCU 160 as may serve a particular application. Hence, FIG. 5 shows (in phantom lines) a second catheter 180', and a second lead 170', having electrodes 172' thereon, also attached to SCU 160. Similarly, the SCUs 160 of FIGS. 3A, 3B, and 3C have outlets 182, 182' for infusing a stimulating drug(s) and electrodes 172, 172' for applying electrical stimulation.

In some examples, the catheters 160 and/or leads 170 are substantially cylindrical. In some alternative examples, one or more of the leads 170 may be paddle-shaped. Electrodes 172, 172' on leads 170, 170' may be arranged as an array, for instance, as two or more collinear electrodes, or even as four or more collinear electrodes, or they may not be collinear. A tip electrode may also be supplied at the distal end of one or more leads.

In some examples, SCU 160 is programmable to produce either monopolar electrical stimulation, e.g., using the SCU case as an indifferent electrode, or bipolar electrical stimulation, e.g., using one of the electrodes of the electrode array as an indifferent electrode. In some examples, the SCU 160 may have at least four channels and drive up to sixteen or more electrodes.

As shown in FIG. 5, SCU 160 may additionally or alternatively include electronic circuitry 154 for receiving data and/or power from outside the body by inductive radio frequency (RF), or other electromagnetic coupling. To this end, electronic circuitry 154 may include an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

In some examples, electronic circuitry 154 includes a processor and/or other components configured to generate one or more stimulation pulses that are applied to a patient 208 through electrodes 172 in accordance with one or more stimulation parameters stored in a programmable memory unit 164. Additionally or alternatively, the processor may be configured to control stimulation parameters associated with drug stimulation. For example, the processor may be configured to cause the SCU 160 to vary the rate of infusion (e.g., intermittent infusion, infusion at a constant rate, and bolus infusion).

As mentioned, SCU 160 may also include a programmable memory 164 for storing one or more sets of data and/or stimulation parameters. Among other things, memory 164 may allow electrical and/or drug stimulation to be adjusted to settings that are safe and efficacious with minimal discomfort for each individual. Specific parameters may provide therapeutic advantages for various types and severities of movement disorders. For instance, some patients may respond favorably to intermittent stimulation, while others may require continuous treatment for relief. In some examples, electrical and drug stimulation parameters are controlled independently, e.g., continuous electrical stimulation and no drug stimulation. However, in some instances, they may advantageously be coupled, e.g., electrical stimulation may be programmed to occur only during drug infusion.

In addition, different stimulation parameters may have different effects on neural tissue. Therefore, parameters may be chosen to target specific neural populations and/or to exclude others, or to increase neural activity in specific neural populations and/or to decrease neural activity in others. For example, relatively low levels of stimulation current (e.g., anywhere between about 0.05 mA to about 5.0 mA) are likely to recruit only relatively large diameter fibers. In some examples, the stimulation may be configured to selectively increase neural activity of only the relatively large diameter fibers of NTS 100. Relatively low amplitude electrical current pulses are likely to produce such selective excitation.

As another example, relatively low frequency neurostimulation (i.e., less than about 100-150 Hz) typically has an excitatory effect on surrounding neural tissue, leading to increased neural activity, whereas relatively high frequency neurostimulation (i.e., greater than about 100-150 Hz) may have an inhibitory effect, leading to decreased neural activity. Similarly, excitatory neurotransmitters (e.g., glutamate, dopamine, norepinephrine, epinephrine, acetylcholine, serotonin), agonists thereof (e.g., glutamate receptor agonist(s), apomorphine), and agents that act to increase levels of an excitatory neurotransmitter(s) (e.g., edrophonium, Mestinon) generally have an excitatory effect on neural tissue, while inhibitory neurotransmitters (e.g., dopamine, glycine, and gamma-aminobutyric acid, a.k.a. GABA), agonists thereof (e.g., muscimol, apomorphine), and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. prazosin, metoprolol, atropine, benztropine) and agents that decrease levels of excitatory neurotransmitter(s) (e.g., acetylcholinesterase, Group II metabotropic glutamate receptor (mGluR) agonists such as DCG-IV) may inhibit neural activity.

The SCU 160 may also include a power source 166. In some examples, the power source 166 may include a self-contained power source utilizing any suitable means of generation or storage of energy (e.g., a primary battery, a replenishable or rechargeable battery such as a lithium ion battery, an electrolytic capacitor, a super- or ultra-capacitor, or the like), a rechargeable power source, and/or means receiving power from an external power source. In cases where the power source 166 includes a rechargeable power source, the SCU 160 may be configured to receive power from an external battery charging system (EBCS) 192, typically through an inductive link 194.

In some examples, the SCU 160 operates independently. Alternatively, the SCU 160 operates in a coordinated manner with other SCU(s), other implanted device(s), and/or other device(s) external to the patient's body. For instance, an SCU 160 may control or operate under the control of another implanted SCU(s), other implanted device(s), and/or other device(s) external to the patient's body. An SCU may communicate with other implanted SCUs, other implanted devices, and/or devices external to a patient's body via, e.g., an RF link, an ultrasonic link, a thermal link, and/or an optical link. Specifically, an SCU may communicate with an external remote control (e.g., patient and/or physician programmer) that is configured to send commands and/or data to an SCU and that may also be capable of receiving commands and/or data from an SCU.

For example, the SCU 160 may be activated, deactivated, programmed, and/or tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through RF link 196, or indirectly through IR link 198, HHP 200, and RF link 195.

Figure 6:
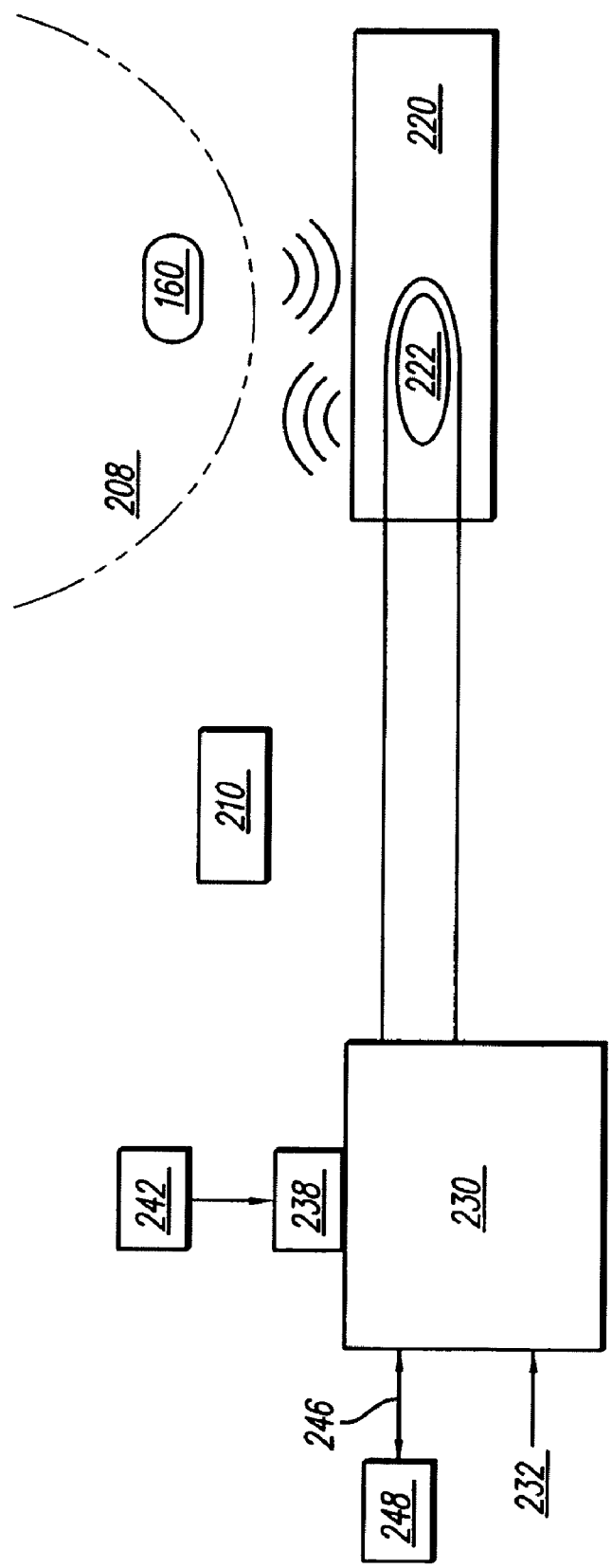
FIG. 6 illustrates various external components of a system control unit according to principles described herein.

External components for programming and/or providing power to the SCU 160 are also illustrated in FIG. 6. When communication with such an SCU 160 is desired, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these examples, manual input means 238 includes various electromechanical switches and/or visual display devices that provide the patient and/or caregiver with information about the status and prior programming of SCU 160.

In some examples, the patient 208 switches SCU 160 on and off by use of controller 210, which may be handheld. SCU 160 is operated by controller 210 by any of various means, including sensing the proximity of a permanent magnet located in controller 210, sensing RF transmissions from controller 210, or the like.

Additionally or alternatively, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, hat, or the like. Other possibilities exist, including a head band, patch, or other structure(s) that may be affixed to the patient's body or clothing. External appliances may include a package that can be, e.g., worn on the belt, may include an extension to a transmission coil affixed, e.g., with a Velcro® band or an adhesive, or may be combinations of these or other structures able to perform the functions described herein.

In order to determine the strength and/or duration of electrical stimulation and/or the amount and/or type(s) of stimulating drug(s) required to produce the desired effect, a patient's response to and/or need for treatment may be sensed. For example, head acceleration, electrical activity of the brain (e.g., EEG or discharge frequency of a neural population), nerve activity (e.g., ENG), muscle activity (e.g., limb EMG), or other activity may be sensed.

For instance, one or more electrodes may be used for recording electrical signals from the brain. Recording of the neural activity of one or more areas being stimulated, e.g., NTS 100 or pallido-subthalamic tracts 106, may be performed in order to determine the discharge frequency of the neural population. This sensing may occur during stimulation or during a temporary suspension of stimulation. In some examples, the amplitude of stimulation is increased if the discharge frequency is above a programmable threshold frequency, and the amplitude of stimulation is decreased if the discharge frequency is less than another programmable threshold frequency. The two programmable threshold frequencies may be the same or may be different in order to achieve hysteresis.

In another example, one or more accelerometers may be used for sensing acceleration of the head. Rhythmic acceleration of the head is seen in head tremor. Thus, the amplitude of rhythmic head acceleration is an indicator of the amplitude of head tremor. The amplitude of stimulation is increased if the amplitude of rhythmic head acceleration is above a programmable threshold amplitude, and the amplitude of stimulation is decreased if the amplitude of rhythmic head acceleration is below a programmable threshold amplitude. The two programmable threshold amplitudes may be the same or may be different in order to achieve hysteresis. This sensing may advantageously be used for patients with significant head tremor as a component of their movement disorder, such as certain patients with benign essential tremor.

Other measures of the state of the patient may additionally or alternatively be sensed. For instance, one or more neurotransmitter levels, their associated breakdown product levels, hormone levels, or other substances, such as dopamine levels, interleukins, cytokines, lymphokines, chemokines, growth factors, electrolytes, enzymes, medication, and/or other drug levels, or levels of any other bloodborne substance(s), and/or changes in one or more of these may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). For example, when electrodes of SCU 160 are implanted in or adjacent to pallido-subthalamic tracts 106, a stimulating electrode of SCU 160, or other sensing means contained in the electrode lead, catheter, IPG, microstimulator, or any part of the system may be used to sense changes in neural firing frequency of the pallido-subthalamic tracts 106 resulting from the electrical and/or drug stimulation applied to the pallido-subthalamic tracts 106. (As used herein, "adjacent" or "near" means as close as reasonably possible to targeted tissue, including touching or even being positioned within the tissue, but in general, may be as far as about 150 mm from the target tissue.)

Alternatively, an SCU dedicated to sensory processes communicates with an SCU providing stimulation pulses. The implant circuitry 154 may, if necessary, amplify and transmit these sensed signals, which may be digital or analog. Other methods of determining the required electrical and/or drug stimulation include measuring impedance, acidity/alkalinity (via a pH sensor), muscle EMG, head or limb acceleration (e.g., via accelerometer), EEG, ENG, other methods mentioned herein, and others that will be evident to those of skill in the field upon review of the present disclosure. The sensed information may be used to control stimulation parameters in a closed-loop manner.

For instance, in some examples, a first and second "SCU" are provided. The second "SCU" periodically (e.g. once per minute) records firing rate of neurons in GPi 110 (or the level of a substance, e.g., dopamine or L-Dopa, or an amount of electrical activity, etc.), which it transmits to the first SCU. The first SCU uses the sensed information to adjust electrical and/or drug stimulation parameters according to an algorithm programmed, e.g., by a physician. For example, the amplitude and/or frequency of electrical stimulation may be increased in response to increased firing rate of neurons in GPi 110. In some alternative examples, one SCU performs both the sensing and stimulating functions.

While an SCU 160 may also incorporate means of sensing symptoms or other prognostic or diagnostic indicators of movement disorders, e.g., via sensing of tremor (e.g., via accelerometer), sensing of dopamine or dopamine agonist levels (e.g., L-dopa), and/or sensing of neural electrical activity (e.g., firing rate of neurons in pallido-subthalamic tracts 106), it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback, or the like.

Thus, one or more external appliances may be provided to interact with SCU 160, and may be used to accomplish at least one or more of the following functions:

Function 1: If necessary, transmit electrical power to the SCU 160 in order to power the SCU 160 and/or recharge the SCU 160.

Function 2: Transmit data to the SCU 160 in order to change the stimulation parameters used by the SCU 160.

Function 3: Receive data indicating the state of the SCU 160 (e.g., battery level, drug level, stimulation parameters, etc.).

By way of example, an exemplary method of treating one or more movement disorders (e.g., Parkinson's disease) may be carried out according to the following sequence of procedures. The steps listed below may be modified, reordered, and/or added to as best serves a particular application.

1. A first SCU 160 is implanted so that its electrodes 172 and/or infusion outlet 182 are located in or on or near pallido-subthalamic tracts 106. Electrodes 172' and/or infusion outlets 182' may additionally or alternatively be located in or on or near NTS 100 or putamen to GPi fibers.

2. Using Function 2 described above (i.e., transmitting data) of external electronic appliance 230 and external appliance 220, first SCU 160 is commanded to produce a series of excitatory electrical stimulation pulses, possibly with gradually increasing amplitude, and possibly while infusing gradually increasing amounts of an excitatory neurotransmitter, e.g., glutamate, or an inhibitory neurotransmitter antagonist, e.g., bicuculline.

3. After each stimulation pulse, series of pulses, or at some other predefined interval, any change in, e.g., tremor (sensed, e.g., via accelerometer in limb) resulting from the electrical and/or drug stimulation is sensed, for instance, by one or more electrodes 172, 172' or sensors of a second SCU 160, preferably a microstimulator SCU 160, implanted in or on or near a limb(s). These responses may be converted to data and telemetered out to external electronic appliance 230.

4. From the response data received at external appliance 230 from second SCU 160, or from other assessment, the stimulus threshold for obtaining a response is determined and used by a clinician 242 acting directly 238 or by other computing means 248 to transmit the desired electrical and/or drug stimulation parameters to first SCU 160. Alternatively, the second SCU 160 uses the response data to determine the stimulation parameters and transmits the parameters to first SCU 160. In yet another alternative, the second SCU 160 transmits the response data to first SCU 160, which uses the response data directly to determine the stimulation parameters. Finally, some combination of the above may be used.

5. When patient 208 desires to invoke electrical stimulation and/or drug infusion, patient 208 employs controller 210 to set first SCU 160 in a state where it delivers a prescribed stimulation pattern from a predetermined range of allowable stimulation patterns.

6. To cease electrical and/or drug stimulation, patient 208 employs controller 210 to turn off first SCU 160 and possibly also second SCU 160.

7. Periodically, the patient or caregiver recharges the power source/storage device 166 of first and/or second SCU 160.

In another example, a treatment for movement disorders, e.g., essential tremor, may be carried out according to the following sequence of procedures:

1. An SCU 160 is implanted so that its electrodes 172 and possibly also infusion outlet 182 are located in or on or near NTS 100.

2. First SCU 160 is commanded to produce a series of excitatory electrical stimulation pulses, possibly with gradually increasing amplitude, and possibly while infusing gradually increasing amounts of an excitatory neurotransmitter, e.g., glutamate, or an inhibitory neurotransmitter antagonist, e.g., bicuculline.

3. After each stimulation pulse, series of pulses, or at some other predefined interval, any change in movement disorder signs and symptoms, e.g., change in neural firing rate in GPi 110, resulting from the electrical and/or drug stimulation is sensed, for instance, by one or more of the electrodes 172 of SCU 160. These responses are converted to data and telemetered out to external electronic appliance 230.

4. From the response data received at external appliance 230 from SCU 160, or from other assessment, the stimulus threshold for obtaining a response is determined and is used by a clinician 242 acting directly 238 or by other computing means 248 to transmit the desired electrical and/or drug stimulation parameters to SCU 160.

5. When patient 208 desires to invoke electrical stimulation and/or drug infusion, patient 208 employs controller 210 to set SCU 160 in a state where it delivers a prescribed stimulation pattern from a predetermined range of allowable stimulation patterns.

6. To cease electrical and/or drug stimulation, patient 208 employs controller 210 to turn off SCU 160.

7. Periodically, the patient or caregiver recharges the power source/storage device 166 of SCU 160.

For the treatment of any of the various types and severities of movement disorders, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to, for instance, deal with complex or multiple symptoms or conditions, such as Parkinson's disease coupled with side effects from medication, e.g., dyskinesia.

In some examples a group of two or more SCUs 160 is controlled via closed-loop operation. A need for and/or response to stimulation is sensed via SCU 160, or by an additional SCU (which may or may not be dedicated to the sensing function), or by another implanted or external device. If necessary, the sensed information is transmitted to SCU 160. In some cases, the sensing and stimulating are performed by one SCU. In some examples, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

Figure 7:
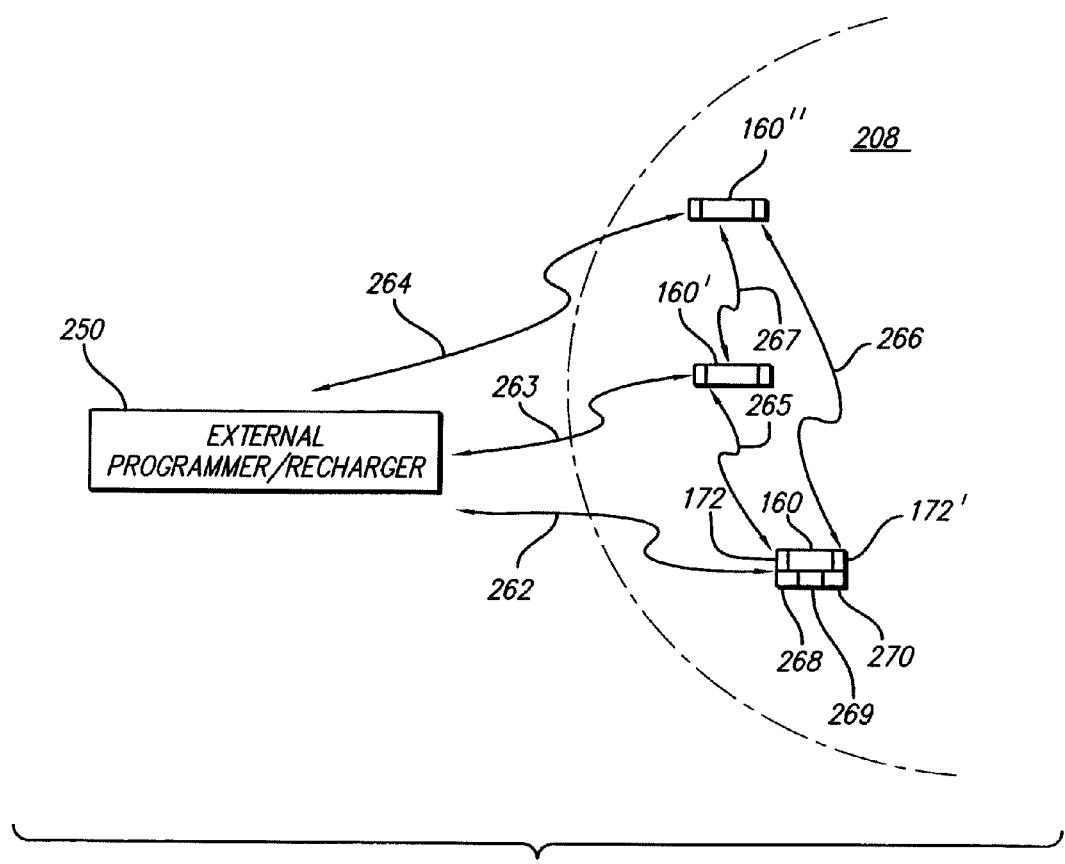
FIG. 7 depicts a system of implantable devices that communicate with each other and/or with external control/programming devices according to principles described herein.

For instance, as shown in the example of FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263 and 264 in FIG. 7. That is, the external controller 250 controls the operation of each of the implanted devices 160, 160' and 160".

In some examples wherein the SCU 160 is configured to infuse one or more drugs at a stimulation site, the SCU 160 may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted SCU 160 and the drug delivery device may be encoded to prevent the accidental or inadvertent delivery of drugs by other signals.

In some examples, the electrical and/or drug stimulation decreases activity of one or more areas of the brain that exhibit chronic increased activity, relative to control subjects, in patients experiencing a movement disorder(s). These areas may include one or more of the pallido-thalamic axons 107, putamen to GPe fibers 108, and/or subthalamo-pallidal fibers. Such inhibitory stimulation is likely to be produced by relatively high-frequency electrical stimulation (e.g., greater than about 100-150 Hz), an excitatory neurotransmitter antagonist(s) (e.g. prazosin, metoprolol, atropine), an inhibitory neurotransmitter(s) (e.g., GABA), an agonist thereof, an agent that increases the level of an inhibitory neurotransmitter, an agent that decreases the level of an excitatory neurotransmitter (e.g., DCG-IV), a local anesthetic agent (e.g., lidocaine), and/or an analgesic medication. This stimulation may be applied to one or more of the pallido-thalamic axons 107, putamen to GPe fibers 108, and subthalamo-pallidal fibers to treat movement disorder(s).

In some alternative examples, the electrical and/or drug stimulation increases activity of one or more of those areas of the brain that exhibit chronic decreased activity, relative to control subjects, in patients experiencing a movement disorder(s), thereby treating or preventing such disorder(s) and/or the symptoms and/or pathological consequences thereof. These areas may include one or more of the NTS 100, pallido-subthalamic tracts 106, and putamen to GPi fibers. Such excitatory stimulation is likely to be produced by relatively low-frequency electrical stimulation (e.g., less than about 100-150 Hz), an excitatory neurotransmitter (e.g., glutamate, acetylcholine), an excitatory cortical neurotransmitter agonist (e.g., glutamate receptor agonist, L-aspartic acid, N-methyl-D-aspartic acid (NMDA), bethanechol, norepinephrine), an inhibitory neurotransmitter antagonist(s) (e.g., bicuculline), an agent that increases the level of an excitatory neurotransmitter (e.g., edrophonium), and/or an agent that decreases the level of an inhibitory neurotransmitter. This stimulation may be applied to one or more of the NTS 100, pallidosubthalamic tracts 106, and putamen to GPi fibers to treat movement disorder(s).

In some examples, the stimulation selectively increases neural activity of the relatively large diameter fibers of the nucleus tractus solitarius (NTS 100). Relatively low amplitude (e.g., about 0.05 mA to about 5.0 mA) electrical current pulses are likely to produce such selective excitation.

In some examples, one or more stimulating drugs, possibly in combination with electrical stimulation, are infused into the brain. For instance, a growth factor, such as glial cell line-derived neurotrophic factor (GDNF) may be infused into the putamen 116, possibly while providing electrical stimulation as described above. Other stimulating drugs are described previously herein and include brain cell line-derived neurotrophic factor (BDNF), naloxone, and levodopa.

In some examples, sensing means described earlier may be used to orchestrate first the activation of SCU(s) targeting an area(s) of the brain, and then, when appropriate, SCU(s) targeting another area(s) and/or by different means. Alternatively, this orchestration may be programmed, and not based on a sensed condition.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method for treating a movement disorder of a patient, comprising:
   generating a stimulus by a system control unit implanted within the patient; and
   applying the stimulus to a stimulation site of the patient in accordance with one or more stimulation parameters to increase neural activity of the stimulation site, wherein the stimulation site comprises one of a nucleus tractus solitarius, pallido-subthalamic tracts, and putamen to GPi fibers, thereby treating the movement disorder of the patient.

2. The method of claim 1, wherein the stimulus comprises an electrical current.

3. The method of claim 2, wherein the electrical current has an amplitude in the range of 0.05 milliamps to 5.0 milliamps, and a frequency less than 100 Hertz.

4. The method of claim 1, wherein the stimulus comprises one or more drugs.

5. The method of claim 4, wherein the one or more drugs comprises at least one or more of an excitatory neurotransmitter, an excitatory cortical neurotransmitter agonist, an inhibitory neurotransmitter antagonist, an agent that increases the level of an excitatory neurotransmitter, and an agent that decreases the level of an inhibitory neurotransmitter.

6. The method of claim 1, further comprising:
   sensing at least one condition related to the movement disorder; and
   adjusting the one or more stimulation parameters based on the at least one sensed condition.

7. The method of claim 1, wherein the system control unit is implanted entirely within the brain of the patient.

8. The method of claim 1, further comprising storing the one or more stimulation parameters in a programmable memory unit.

9. The method of claim 1, wherein the stimulation site comprises the nucleus tractus solitarius.

10. The method of claim 1, wherein the stimulation site comprises the pallido-subthalamic tracts.

11. The method of claim 1, wherein the stimulation site comprises the GPi fibers.

12. A method for treating a movement disorder of a patient, comprising:
   generating a stimulus by a system control unit implanted within the patient; and
   applying a stimulus to a stimulation site of the patient in accordance with one or more stimulation parameters to decrease neural activity of the stimulation site, wherein the stimulation site comprises one of pallido-thalamic axons, putamen to GPe fibers, and subthalamo-pallidal fibers, thereby treating the movement disorder of the patient.

13. The method of claim 12, wherein the stimulus comprises an electrical current.

14. The method of claim 13, wherein the electrical current has a frequency equal to or greater than 100 Hertz.

15. The method of claim 12, wherein the stimulus comprises one or more drugs.

16. The method of claim 12, further comprising:
   sensing at least one condition related to the movement disorder; and
   adjusting the one or more stimulation parameters based on the at least one sensed condition.

17. The method of claim 12, wherein the system control unit is implanted entirely within the brain of the patient.

18. The method of claim 12, further comprising storing the one or more stimulation parameters in a programmable memory unit.

19. The method of claim 12, wherein the stimulation site comprises the pallido-thalamic axons.

20. The method of claim 12, wherein the stimulation site comprises the putamen to GPe fibers.

21. The method of claim 12, wherein the stimulation site comprises the subthalamo-pallidal fibers.

* * * * *